United States Patent
Arita et al.

(10) Patent No.: US 11,779,205 B2
(45) Date of Patent: Oct. 10, 2023

(54) IMAGE CLASSIFICATION METHOD, DEVICE, AND PROGRAM

(71) Applicant: KOWA COMPANY, LTD., Aichi (JP)

(72) Inventors: Reiko Arita, Saitama (JP); Katsumi Yabusaki, Higashimurayama (JP)

(73) Assignee: KOWA COMPANY, LTD., Aichi (JP)

( * ) Notice: Subject to any disclaimer, the term of this patent is extended or adjusted under 35 U.S.C. 154(b) by 700 days.

(21) Appl. No.: 16/976,375

(22) PCT Filed: Mar. 1, 2019

(86) PCT No.: PCT/JP2019/008000
§ 371 (c)(1),
(2) Date: Aug. 27, 2020

(87) PCT Pub. No.: WO2019/168142
PCT Pub. Date: Sep. 6, 2019

(65) Prior Publication Data
US 2021/0212561 A1 Jul. 15, 2021

(30) Foreign Application Priority Data
Mar. 2, 2018 (JP) ................................. 2018-037218

(51) Int. Cl.
*A61B 3/10* (2006.01)
*A61B 3/00* (2006.01)
(Continued)

(52) U.S. Cl.
CPC ............ *A61B 3/101* (2013.01); *A61B 3/0025* (2013.01); *A61B 3/1015* (2013.01); *A61B 3/14* (2013.01);
(Continued)

(58) Field of Classification Search
None
See application file for complete search history.

(56) References Cited

U.S. PATENT DOCUMENTS 9,028,065 B2 * 5/2015 Yokoi .................. A61B 3/101
351/205
2012/0300174 A1 * 11/2012 Yokoi .................. A61B 3/101
382/128
(Continued)

FOREIGN PATENT DOCUMENTS

EP 3466319 A1 4/2019
JP 3556033 B2 8/2004
(Continued)

OTHER PUBLICATIONS

International Search Report and Written Opinion issued in International Patent Application No. PCT/JP2019/008000, dated May 28, 2019; with partial English translation.

*Primary Examiner* — Dov Popovici
(74) *Attorney, Agent, or Firm* — McDermott Will & Emery LLP (57) ABSTRACT

In classifying images by machine learning, provided are an image classification method, device, and program for classifying the image from which the feature difference is hardly detected, in particular, classifying the interference fringe image of tear fluid layer by the dry eye types. The method includes a step of acquiring a feature value from an interference fringe image of tear fluid layer for learning, a step of constructing a model for classifying an image from the feature value acquired from the interference fringe image of tear fluid layer for learning, a step of acquiring the feature value from an interference fringe image of tear fluid layer for testing, and a step of performing classification processing for classifying the interference fringe image of tear fluid layer for testing by types of dry eye using the model and the feature value acquired from the interference fringe image of tear fluid layer.

12 Claims, 6 Drawing Sheets

(51) Int. Cl.
*A61B 3/14* (2006.01)
*G06V 10/75* (2022.01)
*G06F 18/24* (2023.01)
*G06V 10/25* (2022.01)
*G06V 40/16* (2022.01)

(52) U.S. Cl.
CPC .............. *G06F 18/24* (2023.01); *G06V 10/25* (2022.01); *G06V 10/758* (2022.01); *G06V 40/16* (2022.01)

(56) References Cited

U.S. PATENT DOCUMENTS

2016/0270656 A1    9/2016   Samec et al.
2020/0154995 A1*   5/2020   Yabusaki ............... A61B 3/101

FOREIGN PATENT DOCUMENTS

| | | |
|---|---|---|
| JP | 2009-258953 A | 11/2009 |
| JP | 2011-156030 A | 8/2011 |
| JP | 5176773 B2 | 4/2013 |
| WO | 2016/149416 A1 | 9/2016 |
| WO | 2017/209024 A1 | 12/2017 |
| WO | 2019/009277 A1 | 1/2019 |

\* cited by examiner

| | | | | | | | |
|---|---|---|---|---|---|---|---|
|155|152|152|156|155|154|152|151|
|155|154|151|158|153|159|158|152|
|156|158|153|157|157|156|151|153|
|153|151|158|153|152|151|154|156|
|158|151|152|158|143|144|151|156|
|155|153|158|151|141|145|159|157|
|153|151|159|158|156|157|156|155|
|159|153|154|152|153|155|152|156|

REGION 1 — PIXEL OF INTEREST 1
PIXEL OF INTEREST 2
REGION 2

B

| | | | | | | | |
|---|---|---|---|---|---|---|---|
|1.4|1.7|2.7|2.6|2.3|2.8|3.4|3.2|
|2.0|2.2|2.7|2.5|1.9|2.7|3.0|2.6|
|2.4|2.6|3.0|2.8|2.9|3.0|3.0|2.6|
|3.3|3.0|3.1|4.7|5.6|4.8|3.8|2.3|
|2.7|3.0|3.2|6.2|5.6|5.9|5.3|2.7|
|2.7|3.2|3.6|6.8|7.1|7.0|5.5|2.7|
|2.8|3.0|3.2|5.5|5.7|5.9|4.1|2.3|
|3.5|3.4|3.3|2.8|2.3|1.9|1.7|1.9|

IMAGE CLASSIFICATION METHOD, DEVICE, AND PROGRAM

CROSS-REFERENCE OF RELATED APPLICATIONS

This application is the U.S. National Phase under 35 U.S.C. § 371 of International Patent Application No. PCT/JP2019/008000, filed on Mar. 1, 2019, which in turn claims the benefit of Japanese Application No. 2018-037218, filed on Mar. 2, 2018, the entire disclosures of which Applications are incorporated by reference herein.

TECHNICAL FIELD

The present invention relates to an image classification method, a device and a program therefor.

BACKGROUND

The eyeball and the eyelid are protected by a tear fluid from entry of a foreign matter, drying, a damage caused by friction, and the like. A tear fluid layer is composed of two layers, a liquid layer including water that occupies most of the tear fluid layer and a glycoprotein (mucin), and a lipid layer covering the liquid layer. The lipid layer prevents evaporation of the water content of the liquid layer by preventing the liquid layer from being in direct contact with the air component of the lipid layer is secreted from the Meibomian gland present in the eyelid. If the Meibomian gland is damaged due to aging, inflammation, scratching, and the like, the lipid layer is not properly formed, causing a symptom, so-called dry eye, due to failure to maintain the liquid layer.

Dry eye can be classified into an "Aqueous deficient dry eye (ADDE)" and an "Evaporative dry eye (EDE)." In outlining each type, the "ADDE" is a type in which the water content of the liquid layer becomes insufficient because of, for example, a reduction in the secreted tear fluid amount. The "EDE" is a type of dry eye caused by enhanced evaporation of the water content of the liquid layer due to lack of the lipid layer.

Diagnosis of the dry eye disease is conventionally performed by using an interference fringe image of tear fluid layer obtained by imaging the cornea of a subject. As described above, the cornea is covered with the tear fluid layer composed of the lipid layer and the liquid layer, and thus an interference fringe caused by the tear fluid appears in the captured image. The interference fringe of tear fluid layer shows certain predefined features depending on healthy person and dry eye types, and thus these features are used for diagnosing the dry eye disease.

As an ophthalmic apparatus for acquiring the interference fringe image of tear fluid layer, for example, a technique described in Patent Literature 1 or the like has been known. Further, Patent Literature 2 describes a device, a method, and the like relating to image recognition and image classification by machine learning, which are commonly available in recent years.

As a method of the machine learning relating to image recognition and image classification, a method called "Bag of Visual Words," "Bag of Features," "Bag of Keypoints," or the like has been known.

The main image recognition and classification method by this technique generally includes the following procedures: "1. extracting local feature value from feature point in image for learning," "2. creating "visual words" by clustering local feature values," "3. performing vector quantization of local feature values," "4. displaying vector-quantized feature values in histogram by "visual words," and "5. classifying by classifier."

Specifically, a local feature value is first extracted from a feature point in an image for learning. The local feature value includes gradient (vector) information appearing as an edge or a corner of the feature point Examples of a method for determining the local feature point in the image include a method of setting a region range and position randomly or in a fixed manner, and a method in which the image for learning is smoothed on the basis of a plurality of scales and a region showing a feature such as an edge or a corner in the image is determined as the feature point by obtaining a difference between each scale after smoothing.

The local feature values thus obtained are clustered to create "visual words dictionary" (also referred to as "code book"). As a representative method of clustering, the k-means method is known.

Next, the local feature value extracted from the feature point in the image for learning is subjected to vector quantization and displayed in a histogram based on the created "visual word." Information displayed in the histogram represents the feature information (feature vector) of the image.

Basically, the same processes as described above are performed to classify an image (test image) Information displayed in the histogram of the test image created as a final product represents the feature information of the test image. This makes it possible to classify the image by a classifier on the basis of the feature information accumulated for learning and the feature information of the test image. As the classifier (classification method), for example, as described in Patent Literature 2 and Patent Literature 3, various techniques such as support vector machine and earth mover's distance (EMD) have been proposed.

CITATION LIST

Patent Literature

Patent Literature 1: Japanese Patent No. 3556033
Patent Literature 2: Japanese Patent Application Laid-Open No. 2009-258953
Patent Literature 3: Japanese Patent No. 5176773
Patent Literature 4: International Publication No. 2019009277

SUMMARY OF INVENTION

Technical Problem

The image classification using common machine learning has been described above. When the types of the dry eye are classified using the interference fringe image of tear fluid layer, it is very difficult to obtain a desired result by a conventional and general image classification method.

As reason for this, it is speculated that, when the interference fringe image of tear fluid layer is classified by the types of the dry eye, the extracted feature point and the feature value obtained therefrom do not necessarily represent the feature to be focused for performing the classification by the types of the dry eye.

For example, in an image of a car, a classical guitar, or the like, a difference in the outline, the color, or the like can be strongly detected as a feature difference, making the feature information for the image classification self-evident. As a result, the classification can be performed with high accuracy. However, a basic structure or pattern is not observed in the interference fringe image of tear fluid layer, and thus, a large feature difference is not observed in many cases. This causes a problem in which the feature point is not set to the feature to be originally focused or a proper feature value cannot be extracted in the interference fringe image of tear fluid layer.

Further, the conventional classification by the dry eye types largely depends on knowledge or experience of an observer such as an ophthalmologist and is thus influenced by subjectivity such as the knowledge or the experience of the observer. Consequently, there is a demand for a method, a device, or the like that assists objective and steady classification with little bias caused by the observer as described above.

Solution to Problem

The present invention has been made in view of the foregoing conventional problems and provides an image classification method, device, and program including the following steps or means.
(1) The invention includes a step of acquiring a feature value from an interference fringe image of tear fluid layer for learning, a step of constructing a model for classifying an image from the feature value acquired from the interference fringe image of tear fluid layer for learning, a step of acquiring the feature value from an interference fringe image of tear fluid layer for testing, and a step of performing classification processing for classifying the interference fringe image of tear fluid layer for testing by types of dry eye using the model and the feature value acquired from the interference fringe image of tear fluid layer for testing.
(2) In the (1) described above, the feature value is information relating to a color of the image and includes at least one piece of information relating to a color, color diversity, color brightness, and local color variation.
(3) In the (2) described above, the information relating to the color is information based on a luminance average of at least one of red and blue luminance images.
(4) In the (2) or (3) described above, the information relating to the color diversity is information based on a standard deviation of a luminance of at least one of the red and blue luminance images.
(5) In any of the (2) to (4) described above, the information relating to the color brightness is information based on a difference value of luminances of pixels.
(6) In any of the (2) to (5) described above, the local color variation is information based on a standard deviation calculated from a luminance of a pixel of interest and a luminance of a pixel adjacent thereto.
(7) In any of the (1) to (6) described above, in a case where the interference fringe image of tear fluid layer for testing is a moving image, a plurality of predetermined frames are subjected to the classification processing and the most frequent result is regarded as a classification result of the image for testing.
(8) In any of the (1) to (7) described above, the feature value is acquired from a predetermined region of the interference fringe image of tear fluid layer for learning and the interference fringe image of tear fluid layer for testing.
(9) In any of the (1) to (8) described above, the interference fringe image of tear fluid layer is a moving image within a predetermined period of time subsequent to eyelid-opening detection or one or more still images acquired at an optional timing within a predetermined period of time subsequent to eyelid-opening detection.
(10) In the (9) described above, the predetermined period of time is 5 seconds.

Advantageous Effects of Invention

In the present invention, the image is classified by the machine learning using the information indicating the color, the color diversity, the color brightness, the local color variation, and the like of the image as the feature value, and thus it becomes possible to classify the image from which the feature difference is hardly detected. For example, it becomes possible to classify the interference fringe image of tear fluid layer by the dry eye types (in particular, "healthy person," "ADDE," and "EDE") Further, in particular, in classifying the interference fringe image of tear fluid layer by the dry eye types, it becomes possible to provide more objective classification index and classification result by excluding subjectivity of an observer as compared with a conventional and general machine learning method. Further, in the present invention, the processing of the present invention is also applied to the image that has been acquired before the collapse of the tear fluid layer is detected, which enables the measurement of the state of the eye in which the tear fluid layer is not completely collapsed. Thus, it can be expected that the very mild collapse, a symptom relating to the collapse, a sign or a tendency of the collapse, or the like can be detected.

DESCRIPTION OF EMBODIMENTS

[Acquisition of Interference Fringe Image of Tear Fluid Layer]

Figure 1:
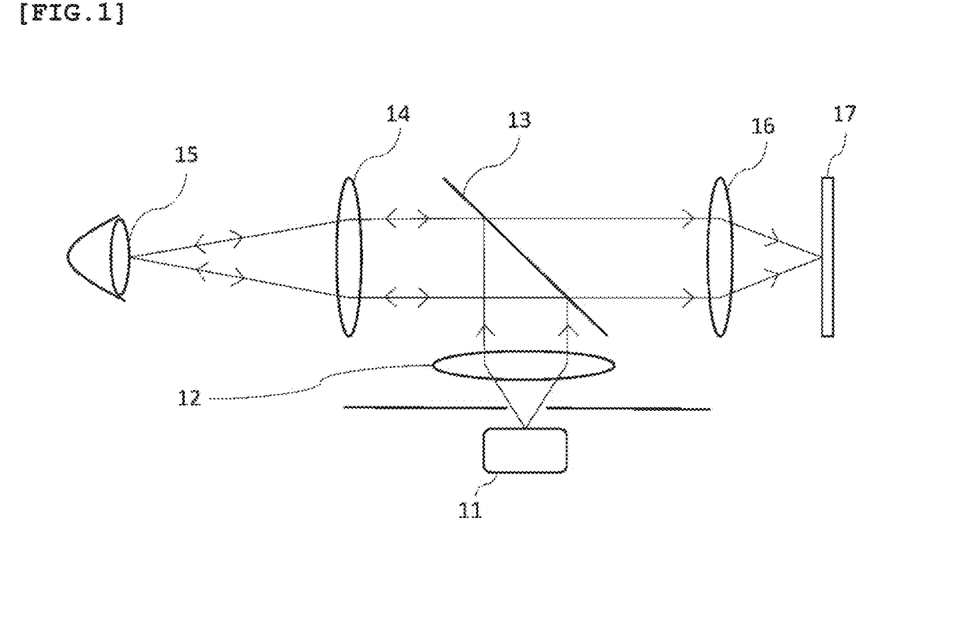
FIG. 1 is a schematic diagram illustrating a configuration of acquiring device for an interference fringe image of tear fluid layer.

As a device for acquiring the interference fringe image of tear fluid layer on a surface of the cornea (acquisition device for interference fringe image of tear fluid layer), a conventionally known device may be appropriately used as long as it can record the captured image as digital data. For example, in the acquisition device for the interference fringe image of tear fluid layer schematically shown in FIG. 1, a light beam, which has been emitted from a light source 11 and transmitted through a diaphragm, sequentially passes through a lens 12, a splitter 13, and an objective lens 14 and is condensed on an anterior eye portion 15 of a subject eye of a subject. Reflected light from the anterior eye portion 15 passes through the objective lens 14 and the splitter 13, so that an image is formed on an imaging element 17 via an imaging lens 16. Captured data of the image formed on the imaging element 17 are subjected to predetermined processing by an image processing engine and converted to still image data and moving image data.

The acquisition device for the interference fringe image of tear fluid layer is connected physically or logically to an image classification device according to the present invention. The image classification device includes a processing unit configured to compute and process data and a storing unit configured to store the image data, moving image data, and other data acquired by the acquisition device for the interference fringe image of tear fluid layer. The storing unit stores a computer program and prescribed data for implementing the present invention, while the processing unit processes data according to a predetermined instruction by the computer program and the like.

Note that, in the following description, the interference fringe image of tear fluid layers include both meaning of moving images composed of a plurality of consecutive frames recorded over a specified time and still images, which are stored in the image classification device itself or a storage device connected thereto.

In this process, regarding acquisition of the interference fringe image of tear fluid layer, acquisition of the interference fringe image of tear fluid layer may be automatically completed after lapse of a predetermined period of time subsequent to the eyelid-opening detection. In particular, in recent years, a diagnosis standard in which the dry eye is diagnosed when "Break Up Time (BUT)," a time from eyelid opening to detection of the collapse of the tear fluid layer, is 5 seconds or shorter is adopted in Asia regions including Japan. Thus, the predetermined period of time is set to 5 seconds and acquisition of the interference fringe image of tear fluid layer may be automatically completed after lapse of 5 seconds subsequent to the eyelid-opening detection.

Further, the interference fringe image of tear fluid layer may be acquired as a still image at a predetermined time interval (for example, in every 0.5 seconds) subsequent to the eyelid-opening detection. Further, the interference fringe image of tear fluid layers are sequentially analyzed, and if the collapse of the tear fluid layer 1 s detected before the lapse of the predetermined period of time, acquisition of the interference fringe image of tear fluid layer may be terminated at that time point. A detailed description will be given below.

For the eyelid-open ng detection, a conventionally known method can be appropriately used. Specifically, for example, the method described in Patent Literature 4 has been known. When the eye blinks, there are usually a significant reduction in the luminance in the image by closing the eyelid and a significant increase in the luminance by opening the eyelid. This method utilizes the significant reduction in the luminance average value by closing the eyelid and the increase in the luminance average value by opening the eyelid during blinking to set a predetermined threshold to the luminance average value and detect a time point when the luminance average value changes to the threshold or more as an eyelid-opening time.

The threshold is preferably set to an average value of the luminances of each color element of RGB in the predetermined region of the image, without being limited thereto. The threshold for the eyelid-opening detection may be set to an optional value, or the eyelid-opening may be detected on the basis of a value which is obtained by appropriately performing an arithmetic operation using the luminances of two or more of the color elements. The luminance of the color image may be directly used, the luminance of the image converted into a gray scale, or the like, may be used.

However, note that the average value of the luminance in the predetermined region is preferably used for the eyelid-opening detection for the purpose of properly setting the threshold. This is because it is difficult to uniformly determine the threshold as the acquired interference fringe images of tear fluid layer do not have a constant level of brightness due to various factors such as the eye state of the subject, for example, the state of the cornea or the amount and length of the eyelashes, and a surrounding light quantity.

For this reason, the average value of the luminance in the predetermined region of the interference fringe image of tear fluid layer is used to set the threshold, so that the proper threshold according to the image can be obtained regardless of the brightness (luminance level) of the image itself. Specifically, a median value of the minimum value and the maximum value of the luminance values obtained from the interference fringe image of tear fluid layer may be set as the threshold or a value obtained by adding a predetermined value to the minimum value or subtracting a predetermined value from the maximum value may be used as the threshold. Any method capable of setting a value within a variation range of the variation of the luminance average value caused by blinking may be used.

As described above, regarding acquisition of the interference fringe image of tear fluid layer, acquisition of the interference fringe image of tear fluid layer may be completed after lapse of the predetermined period of time (for example, 5 seconds) subsequent to the eyelid-opening detection using a timer. Further, if blinking of the subject is detected once or multiple times, acquisition of the interference fringe image of tear fluid layer may be terminated even before the lapse of the predetermined period of time. In almost the same manner as the eyelid-opening detection described above, blinking of the subject may be detected by using a significant change in the luminance between images at the eyelid opening time and the eyelid closing time. Specifically, blinking can be detected by comparing the average value of the luminance in the predetermined region of the image or an optional value, and the predetermined threshold.

Further, as described above, the interference fringe image of tear fluid layer is acquired as a still image at the predetermined time interval (for example, in every 0.5 seconds) subsequent to the eyelid-opening detection, and, by sequentially analyzing whether the collapse of the tear fluid layer can be detected in these images, acquisition of the interference fringe image of tear fluid layer may be terminated at the time point when the collapse of the tear fluid layer is detected. In this process, the collapse of the tear fluid layer can be detected by appropriately using a conventionally known method, for example, a commonly used edge detection method or Hough transform method. However, in the present example, a description will be given using the method described in Patent Literature 4. In this method, a value indicating color variation in the interference fringe image of tear fluid layer is calculated and evaluated. Specifically, this method examines the luminance in the RGB color space of the interference fringe image of tear fluid layer in each pixel in a predetermined region of the image and evaluates which extent the intensity of at least one or more of the color elements of red, green, and blue varies in the region. A detailed description will be given below.

As the color variation, a variance, a deviation (a standard deviation, etc.) obtained from the luminance of each color element, or a value (coefficient of variation) obtained by dividing the values of these deviations or standard deviations by an average of luminance of pixel within the region, can be appropriately used. These values may be optionally selected and used as necessary.

The value indicating the color variation may be calculated using the entire image (all pixels). However, it is preferable to obtain the diversity of the color information in a local region in which a pixel of interest and a pixel adjacent thereto are grouped together. The value indicting the color variation thus obtained has a higher resolution despite having lower immediacy of analysis as compared with a case of performing the calculation using the entire image. Further, the spatial position information of such a value is matched with that of the original image, which contributes to identifying a position and an area of the collapse of the tear fluid layer. A detailed description will be given with reference to FIGS. 7A and B.

FIG. 7A is a schematic diagram in which a standard deviation of the luminance is calculated in a region composed of a total of 9 pixels of 3×3 including a pixel of interest and 8 pixels surrounding the pixel of interest in a target, region in an image. Each numerical value in FIG. 7A indicates a numerical value of the luminance in each pixel in a part of the image.

A "region 1" shown in FIG. 7A is composed of a region composed of a total of 9 pixels (3×3 pixels) including a pixel 1 of interest and pixels surrounding the pixel 1 of interest, and a standard deviation in the region 1 is calculated and outputted to the pixel 1 of interest. FIG. 7B shows a result in which the target region in the image having the luminance as shown in FIG. 7A is scanned in this manner.

That is, the target region (entire or a desired part) of the image is scanned using a filter for outputting, to the pixel of interest, the standard deviation of the color information such as luminance in the local region composed of a pixel of interest and predetermined pixels around the pixel of interest as a center, and the standard deviation outputted in each pixel is stored.

Confirming specific numerical values in FIGS. 7A and B, the standard deviation outputted to the pixel 1 of interest in the region 1 is as small as "2.2," while the value outputted to the pixel 2 of interest in the region 2 is as large as "7.1." In principle, the value indicating the color variation tends to be higher as the state of the tear fluid layer is poor. In the data shown in FIG. 3, thus, the color variation is higher in the region 2 than the region 1, making it possible to determine that the state of the tear fluid layer is more deteriorated in the region 2.

Note that, when a subject has a severe symptom of the widespread collapse of the tear fluid layer as indicated by the dry eye severity grade 5, in some cases, the collapse of the tear fluid layer cannot be properly determined solely by the numerical value calculated as the variance or the standard deviation of the color information using the luminance or the like described above. A tear fluid layer collapse site has the constant luminance with small variation as compared with a site where there is no collapse. Thus, when the col lapse site of the tear fluid layer is widespread, there is an increase in the number of sites where the value indicating the variation represented by the variance or the standard deviation described above does not increase. As a result, this may lead to a failure in detecting the tear fluid collapse or erroneous diagnosis as a mild symptom which does not match the actual condition.

Thus, the coefficient of variation calculated by the following "formula 1," that is, a numerical value obtained by dividing the value represented by the variance or the standard deviation of the luminance obtained as described above by the average value of the luminance in the corresponding region may be used.

$$\text{Coefficient of variation} = \text{standard deviation of luminance/luminance average value} \quad (1)$$

Figure 7:
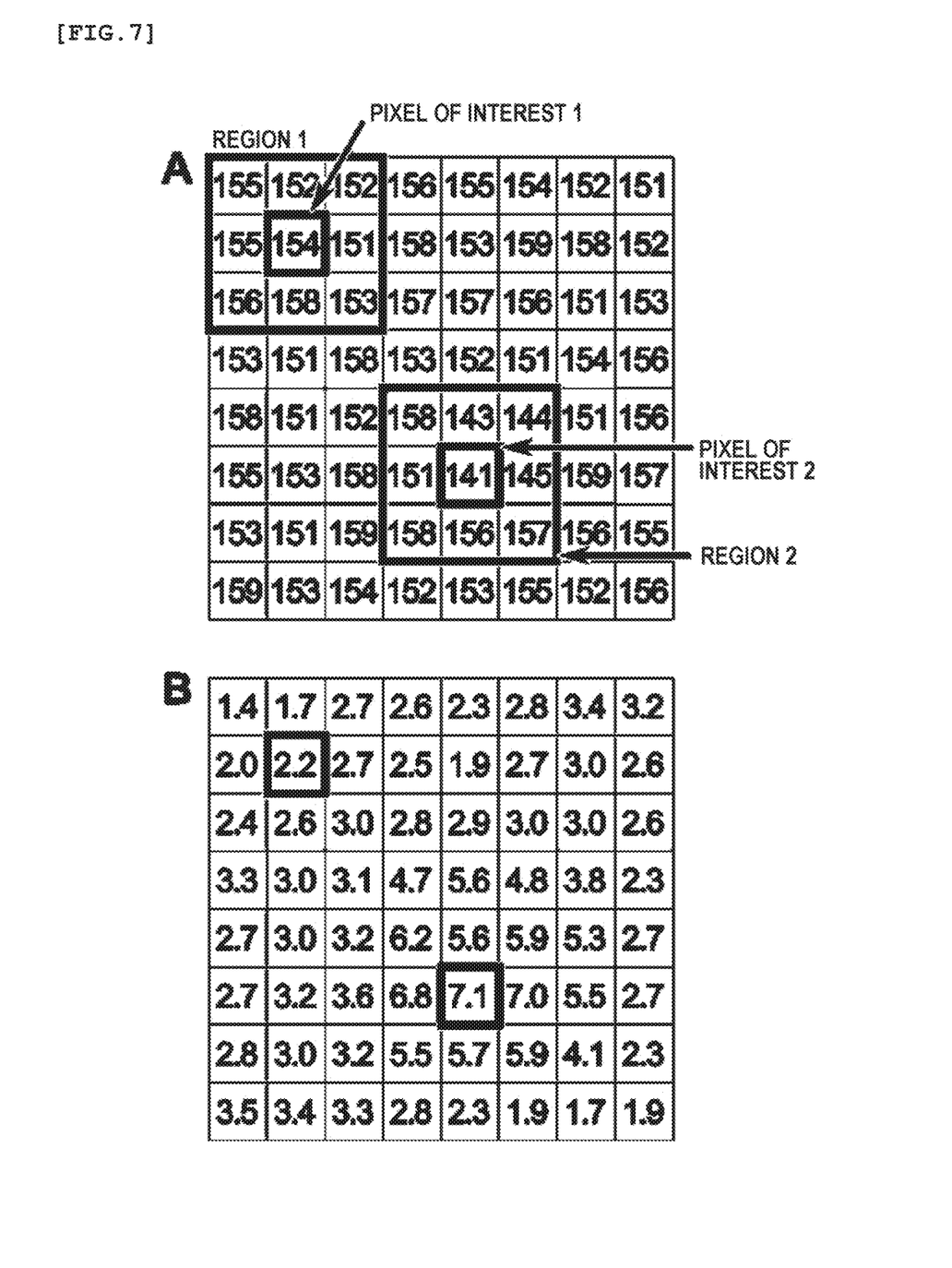
FIG. 7 is diagrams illustrating an example of color information (luminance value) of each pixel in a part of a target region of the interference fringe image of tear fluid layer and an example of a result of calculating standard deviation of a pixel of interest in a predetermined local region.

Note that, in the foregoing description, the value indicating the color variation such as the standard deviation or the coefficient of variation in the local region composed of the pixel of interest and the pixels surrounding the pixel of interest is outputted in each pixel of interest in FIG. 7. However, instead of performing outputting in each pixel of interest, the local region may be regarded as a single section and the standard deviation may be outputted in each section. Further, needless to say, such a region or section is not limited to the total of 9 pixels of 3×3 and may be a group having an optional number of the pixels.

As described above, the value indicating the color variation is obtained by calculating the variation of the color information (luminance, etc.), that is, the variance or the deviation such as the standard deviation in the predetermined region. Further, other than these values, the value obtained by dividing the value indicating the variation of the color information in the predetermined region by the average value of the color information in the predetermined region, that is, the coefficient of variation, is used.

Whether or not the collapse of the tear fluid layer is detected is determined on the basis of the value indicating the color variation such as the variance, the standard deviation, and the coefficient of variation obtained as described above. For example, the number of the pixels or sections of which the value indicating the color variation such as the standard deviation is equal to or higher than a predetermined threshold is counted, and the occurrence of the collapse of the tear fluid layer is determined if the counted number is equal to or higher than a predetermined threshold.

As another method, for example, an area of the pixels or sections of which the value indicating the color variation such as the standard deviation is equal to or higher than a predetermined threshold is calculated, and the occurrence of the collapse of the tear fluid layer may be determined if the area is equal to or higher than a predetermined threshold.

Further, determination may be made on the basis of a ratio of the pixels or sections of which the value indicating the color variation such as the standard deviation is equal to or higher than a predetermined threshold with respect to the entire scanning target region of the extracted image. The occurrence of the collapse of the tear fluid layer may be determined if a ratio of the number or area of the pixels of which the value indicating the color variation is equal to or higher than a predetermined threshold with respect to the number or area of the pixels in the entire scanning target region of the extracted image is equal to or higher than a predetermined level.

However, it is difficult to preclude the possibility that the calculated value indicating the color variation includes a noise due to, for example, the improper original color information of the extracted image. Thus, even if the pixel or section is determined to have the value indicating the color variation of equal to or higher than a predetermined threshold, unless the pixel or section satisfies a predetermined size (area) as one continuous region, such a pixel or section may be excluded.

The foregoing analysis processing for detecting the collapse of the tear fluid layer is applied to the interference fringe image of tear fluid layer acquired as a still image at a predetermined time interval (0.5 seconds) subsequent to the eyelid-opening detection. Then, if it is determined that the coil apse of the tear fluid layer is detected, acquisition of the interference fringe image of tear fluid layer may be terminated at that time point. For example, in a case where the collapse of the tear fluid layer is detected from the interference fringe image of tear fluid layer (still image) after lapse of 0.5 seconds subsequent to the eyelid-opening detection, subsequent acquisition of the interference fringe image of tear fluid layer is suspended. In a case where the collapse of the tear fluid layer is not detected, the interference fringe image of tear fluid layer is further acquired in the following 0.5 seconds (one second after the eyelid-opening detection) and the acquired image is subjected to the analysis processing for detecting the collapse of the tear fluid layer in the same manner. After repeating this procedure, if it is determined that the collapse of the tear fluid layer is not detected after lapse of the predetermined period of time (for example, 5 seconds), acquisition of the interference fringe image of tear fluid layer is completed after the lapse of the predetermined period of time.

The processing of classifying the interference fringe image of tear fluid layer obtained in the foregoing manner by the types of the dry eye will be described below. Regarding the interference fringe image of tear fluid layer used for the classification processing by the types of the dry eye, any or all of the frames of the moving image captured for a predetermined period of time can be subjected to the classification processing. Further, the classification processing may be applied to all of the still images acquired at the predetermined time interval, for example, at an interval of 0.5 seconds, as described above. Alternatively, the classification processing may be applied to either one or both of a still image in which the collapse of the tear fluid layer is detected and a still image immediately preceding that still image. Alternatively, the classification processing may be applied to the still image acquired after lapse of 5 seconds subsequent to the eyelid-opening detection or, in a case of the moving image, the frame acquired after lapse of 5 seconds subsequent to the eyelid-opening detection.

[Color Information of Image]

As the color information usable in the present invention, for example, there is a color information of using three color elements of red, green, and blue (numerical values in an RGB color space), which is used in many electronic image apparatuses. Specifically, the color information in each pixel is luminance of color elements of red, green, and blue included in the pixel.

The following description wall be given on the basis of a case where the luminance in the RGB color space is used, but the color information in the present invention is not limited to the numerical values in the RGB color space. The present invention. does not deny the use of luminance or brightness defined in the HSV color space, the HSB color space, the HIS color space, the HSL color space, or the like.

[Feature Value in Present Invention]

Thus, in the present invention, using the following feature value of the interference fringe image of tear fluid layer makes it possible to improve accuracy of the classification of the interference fringe image of tear fluid layer by the dry eye types using the machine learning. Examples of the feature value usable in the present invention include the following.

(1) Red[AVG]: an image is divided into three layers of the three primary colors of light, and, of these, a luminance image of the red color is used to obtain an average value of the luminance of the pixels in the analysis target region.

(2) Red [SD]: variation of the pixel luminance in the analysis target region of the above-described red color luminance image is obtained as the standard deviation.

(3) Blue [AVG]: the average value is obtained using a blue color luminance image.

(4) Blue [SD]: the standard deviation is obtained using the blue color luminance image.

(5) Diff [AVG]: all pixels in the analysis target region are subjected to the following operations.
 (a) Each luminance value of red, green, and blue in the pixel of interest is obtained.
 (b) A difference value is obtained by subtracting the minimum value of these three values from the maximum value thereof (for example, in a case where the luminance of each color is "red: 192, green: 184, blue: 164," the difference value is "difference value=192−164=28").
 (c) This calculation. is applied to all pixels in the region to obtain a difference image.
 (d) An average value of the pixel luminance in the region is calculated using the obtained image as "Diff [AVG]."

(6) Diff [SD]: The standard deviation of the pixel luminance in the analysis target region is calculated using the difference image obtained in the foregoing (5)-(c).

(7) √Area: using the difference image obtained in the foregoing (5)-(c), the total number of the pixels having the value larger than a certain threshold in the analysis target region is obtained, and the square root of the total number (=area) is calculated.

(8) SD [RED]: the analysis target region of the red color luminance image is subjected to the fall owing operations.
 (a) The variation of the luminance of the pixels included. within a range of the radius R (R is an optional value) from the pixel of interest is obtained as the standard deviation.
 (b) The obtained value is recorded as a value at a site (X, Y coordinates) of the pixel, and this operation is performed in the entire analysis target region to generate a standard deviation. image.
 (c) The variation of the luminance values of the standard deviation image is calculated in the analysis target region of the standard deviation image to obtain SD[RED].

(9) SD[BLUE]: the same processing as in the above-described (8) is performed in the analysis target region of the blue color luminance image to calculate the standard deviation.

(10) Ratio[UPPER]: upper predetermined pixels in the analysis target region are subjected to the following operations.
 (a) The maximum component value and the minimum component value of the luminance values are obtained from the luminance of red, green, and blue of the pixel of interest in the same manner as in the foregoing (5)-(b).

(b) In a case where all of the luminance values of red, green, and blue are equal to or higher than a threshold, the following operation is performed.

Ratio=max/min That is, a value obtained by dividing the obtained maximum value by the minimum value is defined as "Ratio."

(c) The number of the pixels having the Ratio value of greater than a certain threshold is counted as "Ratio [UPPER]."

(11) Ratio[BOTTOM]: lower predetermined pixels in the analysis target region are subjected to the same operations as in the above-described (10) to obtain "Ratio [BOTTOM]."

Figure 2:
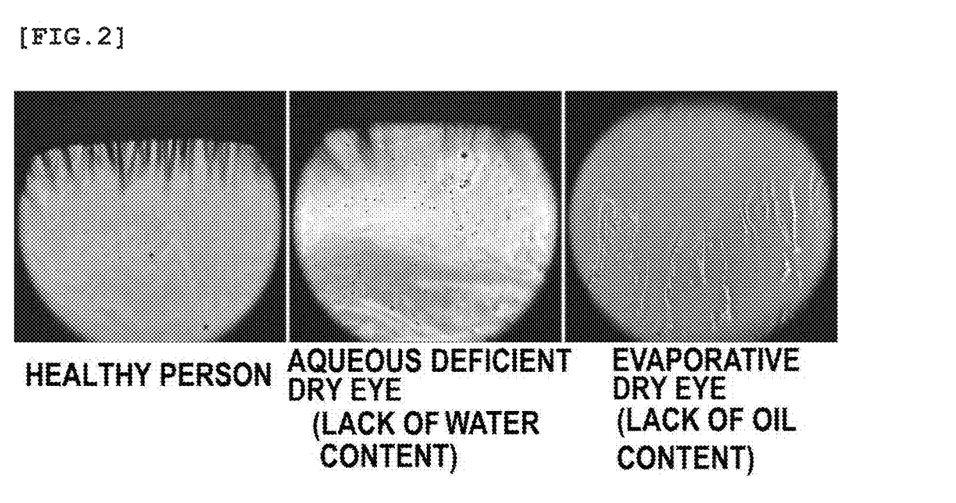
FIG. 2 is an explanatory diagram illustrating an example of interference fringe images of tear fluid layer according to types of dry eye.

Before the meaning of the feature value in the present invention is described, classification of the dry eye will be described in detail. The image classification device according to the present invention mainly focuses on classifying the interference fringe image of tear fluid layer into three patterns of "healthy person," "ADDE," and "EDE." The interference fringe images of tear fluid layer of these three types are shown in FIG. 2. Note that the interference fringe image of tear fluid layer actually acquired is a color image, thus the interference fringe image of tear fluid layer, as well as a color feature thereof and the like, will be described below.

The interference fringe image of tear fluid layer of the "healthy person" generally has little color change on the whole although an interference fringe can be confirmed, and thus it appears as almost a single gray color in contrast, in the "ADDE," although the colors depend on the thickness of the lipid layer, the colors such as red, blue, green, and gray appear in a co-existed manner, and, further, a crack or a defective portion in the tear fluid appears as a bright white color, while a black color partially appears in a linear or dotted pattern so as to form a contour surrounding the crack or the defective portion. The "EDE" appears as a slightly reddish gray color as an overall color, and a crack in the tear fluid partially appears as a white color in a linear pattern.

On the basis of these three feature patterns, the feature value of the present invention will be described. "Red [AVG]" and "Blue [AVG]" are information relating to "color" of the interference fringe image of tear fluid layer and serve as one of indexes for determining a color and brightness of the color. That is, the interference fringe image of tear fluid layer of the healthy person, which exhibits a color close to a relatively bright single gray color with some striped patterns, shows high values both in "Red[AVG]" and "Blue[AVG]," but the difference thereof is small. The interference fringe of tear fluid layer of the "EDE" shows the slightly higher "Red[AVG]" value than that the "Blue [AVG]" value. The interference fringe of tear fluid layer of the "ADDE" shows bright interference colors with a particularly large red color region, and thus the "Red[AVG]" value is higher than that of other dry eye types.

"Red[SD]" and "Blue[SD]" are information indicating "color diversity" of the interference fringe image of tear fluid layer. They basically show the same tendency as seen in the relation of "Red[AVG]" and "Blue[AVG]," but show higher values when a color change in the interference fringe of tear fluid layer is large.

As described above, the four feature values of "Red [AVG]," "Blue[AVG]," "Red[SD]," and "Blue [SD]" are meant to serve as a parameter for generally classifying the dry eye types.

"Diff[AVG]" and "Diff[SD]" indicates a degree of "color brightness" of the interference fringe and shows a larger value with a brighter color. Thus, it is particularly meant to recognize the interference fringe image of tear fluid layer of the "ADDE." "√Area," which similarly uses the difference value of the luminance, is meant to subsidiary improve recognition accuracy of the "ADDE" interference fringe image.

"SD[RED]" and "SD[BLUE]" indicate the variation of the luminance near the pixel of interest, that is, "local variation of color" in the image, thereby causing the following difference. The foregoing "RED[SD]" and "BLUE [SD]" indicate the global variation of the luminance, while "SD[RED]" and "SD[BLUE]" indicate the local variation of the luminance, that is, "SD[RED]" and "SD[BLUE] are strongly influenced by a crack in the tear fluid. The interference fringe image of tear fluid layer of the "healthy person," in which a crack hardly occurs, has small values of these "SD[RED]" and "SD[BLUE]," while the interference fringe images of tear fluid layer of the "ADDE" and the "EDE" have large values thereof. "SD[RED]" and "SD [BLUE] are meant to serve as a parameter which significantly contributes to determining whether or not there is an abnormality such as a crack in the tear fluid.

"Ratio[UPPER]" and "Ratio[BOTTOM]" are the feature values having a function similar to that of the foregoing "Diff[AVG]" and "√Area." In some cases, the interference fringe image of tear fluid layer of the "ADDE" does not show a clear striped pattern or forms a stripe in a small region in an upper or lower portion of the image "Diff [AVG]" and "√Area" targeting the whole analysis target region hardly capture such a local small change, while "Ratio[UPPER]" and "Ratio[BOTTOM]" easily capture such a small change by further narrowing the analysis target region. As a result, "Ratio[UPPER]" and "Ratio[BOTTOM]" are the feature values which contribute to improve the recognition of the "ADDE."

[S1 Determination of Analysis Target Region]

Figure 3:
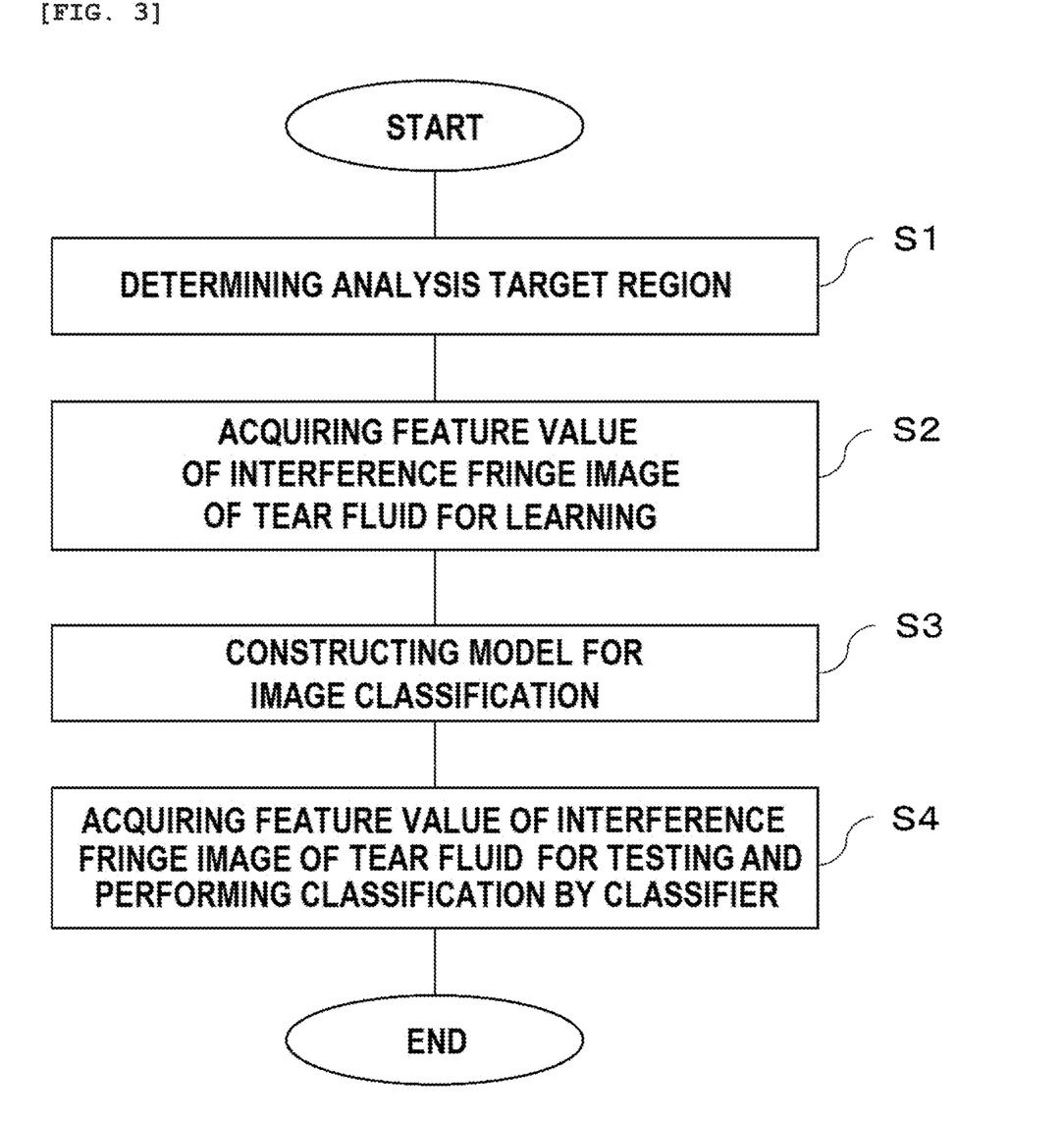
FIG. 3 is a flow diagram illustrating an example of a series of processings according to the present invention.

FIG. 3 shows an example of a series of processings of the image classification of the present invention. The image classification device performs an analysis of an interference fringe image of tear fluid layer of each dry eye type as an image for learning. Since the cornea has the curvature, the interference fringe image of tear fluid layer has a region in which an interference fringe of tear fluid layer appears and a surrounding dark region of which the luminance is significantly low. Thus, it is desirable that this dark region is removed as an unnecessary region and the region in which the interference fringe of tear fluid layer appears (in general, it appears as a substantially circular region in the center of the image) is used as the analysis target region. Further, a deficient proton caused by the eyelid or the eyelash, which often appears particularly in an upper portion of the interference fringe image of tear fluid layer is also desirably removed from the analysis target region as an unnecessary region.

Examples of a specific method for removing the region not needing analysis include, without being bound thereto, a method in which a threshold is set and a pixel of the interference fringe image of tear fluid layer having the luminance of equal to or lower than the threshold is removed from the analysis target. The threshold may be a predetermined fixed value or an unfixed value calculated on the basis of the average value of the luminance of the pixels of the interference fringe image of tear fluid layer or the like. Alternatively, since a boundary between the interference fringe of tear fluid layer and the surrounding black region strongly appears as an edge, a method of determining the analysis target region by detecting this edge may be used.

[S2 Acquisition of Feature Value of Interference Fringe Image of Tear Fluid Layer for Learning]

The image classification device acquires and stores the above-described feature value in the analysis target region of the interference fringe image of tear fluid layer of the "healthy person." In the description above, 11 kinds of the feature values of the present invention are exemplified however, all of them may not be used, or a value obtained by further performing a predetermined arithmetic operation may be adopted as the feature value. As the number of the kinds of the acquired feature values increases, the accuracy of the classification generally improves more. However, considering the processing speed, available resources, and the like, suitable kinds of the feature values may be appropriately selected and acquired.

In this manner, the image classification device acquires the predetermined feature value described above from the interference fringe image of tear fluid. layer of which diagnosis is determined to be the "healthy person" and stores the acquired. feature value. Further, the image classification device acquires the feature values from the interference fringe image of tear fluid layer of the "ADDE" and the interference fringe image of tear fluid layer of "EDE" in the same manner.

[S3 Model Construction for Image Classification]

By performing S2, the predetermined kinds of the feature values and the acquired feature values are correlated and stored. This makes it possible to express the interference fringe image of tear fluid layer by a feature vector having the number of the kinds of the feature values as dimensions. For example, in a case where four kinds of the feature values of "Red[AVG]," "Blue[AVG]," "Red[SD]," and "Blue[SD]" are analyzed and acquired from the interference fringe image of tear fluid layer of a "healthy person," this interference fringe image of tear fluid layer can be expressed by a four-dimensional feature vector defined by these four kinds of quantities.

Having performed the above processing, the image classification device stores and accumulates a plurality of feature vectors relating to the interference fringe image of tear fluid layer of the "healthy person," as well as a plurality of feature vectors relating to the interference fringe image of tear fluid layer of the "ADDE" and a plurality of feature vectors relating to the interference fringe image of tear fluid layer of the "EDE," and thus learns information for the classification by these dry eye types.

Figure 4:
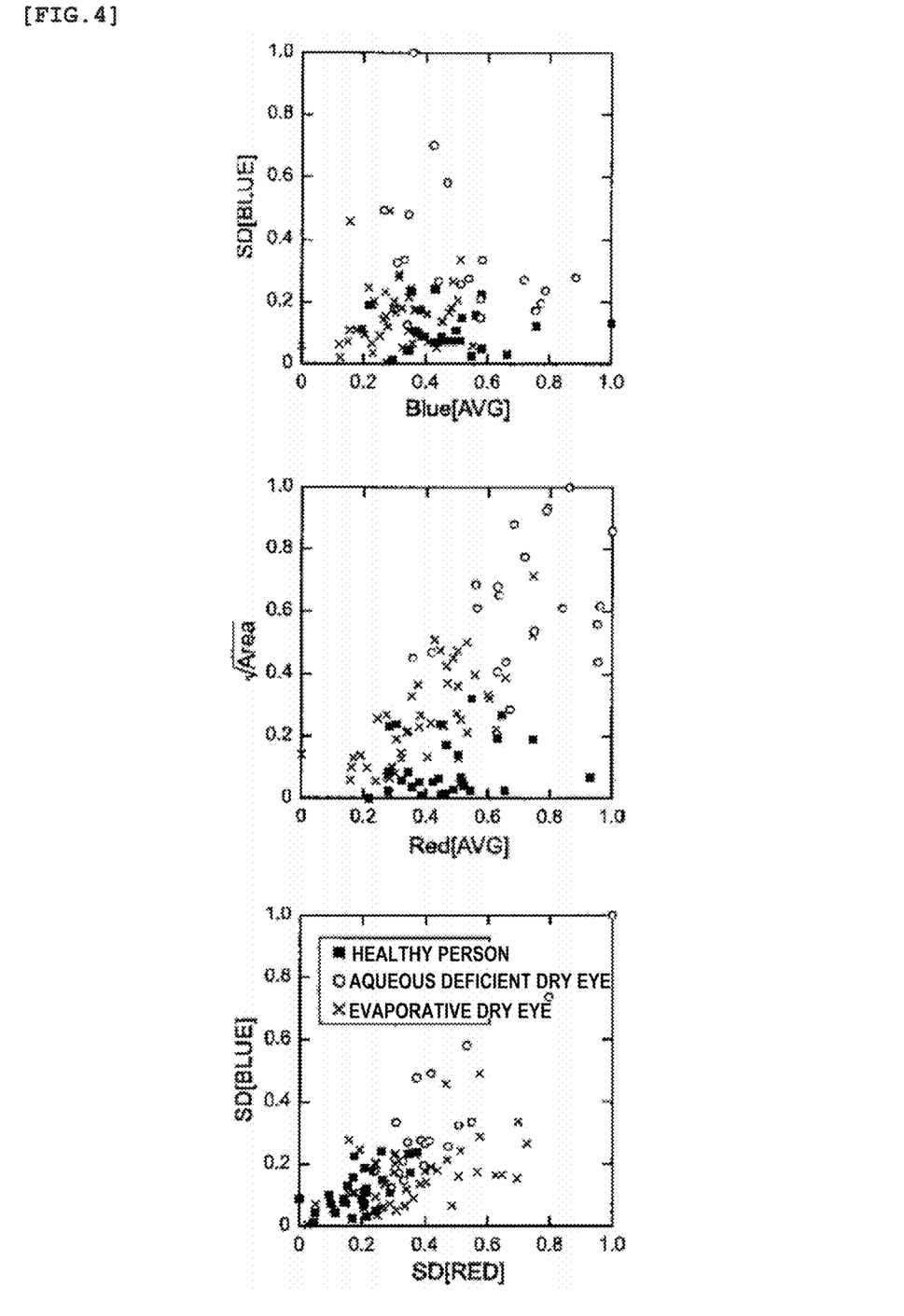
FIG. 4 is a graph illustrating an example of mapping of feature values according to the present invention.

That is, as a result of the foregoing processing, the image classification device recognizes (stores in an identifiable state), among the feature vectors having the above-described feature values as an element, the feature vector indicating the interference fringe of tear fluid layer of the "healthy person," as well as the feature vector indicating the interference fringe of tear fluid layer of the "ADDE" and the feature vector indicating the interference fringe of tear fluid layer of the "EDE." FIG. 4 shows an example of a mapping result of the two-dimensional feature vectors for easy understanding. That is, the interference fringe image of tear fluid layer is the feature vectors in a vector space having the number of the adopted feature values as the number of dimensions, and these feature vectors acquired from the interference fringe image of tear fluid layer for learning serve as a model for determining and classifying images.

[S4 Acquisition of Feature Value of Interference Fringe Image of Tear Fluid Layer for Testing and Classification by Classifier]

The image classification device having undergone the learning processing of S2 and S3 stores the prerequisite information for classifying unknown images as described above and thus can appropriately use a classifier (classification method) that is already generally known such as support vector machine or earth mover's distance (EMD) described above.

As described above, the image classification device has acquired and stored the feature values of the interference fringe image of tear fluid layer for learning in "S2 Acquisition of feature value of interference fringe image of tear fluid layer for learning," and thus it can constitute a model for the image classification using the feature vectors having these feature values as an element.

The image classification device also acquires the predetermined feature values from the interference fringe image of tear fluid layer for testing as in "S2 Acquisition of feature value of interference fringe image of tear fluid layer for learning." The image classification device classifies the interference fringe image of tear fluid layer for testing by the classifier on the basis of the model by the interference fringe image of tear fluid layer for learning and the acquired feature values of the interference fringe image of tear fluid layer for testing.

EXAMPLES

Comparative Example 1

As Comparative example 1, "Bag of visual words method" commonly used as an image classification method by machine learning is used to evaluate the dry eye type classification method using the interference fringe image of tear fluid layer. As the interference fringe images of tear fluid layer used in Comparative example 1, 46 images (still images) of each type of the dry eye (healthy person, ADDE, and EDE), a total of 138 images, were prepared. These interference fringe images of tear fluid layer were divided into two groups so that 31 images of each type (total of 93 images) were used for learning and 15 images of each type (total of 45 images) were used for testing. Then, the image classification device performed the learning as described above.

In order to avoid that the quality of the result of the correct value caused by a combination of files selected by chance influenced the evaluation of the established model, a trial in which 311 images for learning of each type were randomly selected and the remaining 15 images were used as the images for testing for evaluation was performed a total of 10 times, and the average value thereof was used to determine the quality of the model.

The classification result described above is shown F-measure is commonly known as one of statistical measures for measuring reliability of the model and is calculated as follows.

F-measure=2×precision×recall/(precision+recall)

The concrete numerical values of F-measure in the present Comparative example are as follow, healthy person: 0.587, ADDE: 0.669, and EDE: 0.549. Further, in Comparative example 1, a coincidence was eliminated. The kappa coefficient, calculated as true agreement with a diagnostic result by a doctor was 0.367, indicating that the image classification model by the general machine learning was not effective in the present case.

Example 1

As the interference fringe images of tear fluid layer used in Example 1, the same image set as used in Comparative example 1 was used. The images were divided into two groups by the method described in Comparative example 1, and the image classification device performed the learning in the same manner as in the foregoing Comparative example 1 by dividing 46 images (still images) of each type of the dry eye (healthy person, ADDE, and EDE), a total of 138 interference fringe images of tear fluid layer, into two groups, 31 images of each type (total of 93 images) used for learning and 15 images of each type (total of 45 images) used for testing.

As the feature values used in Example 1, all 11 kinds of the feature values described above ("Red[AVG]," "Red[SD]," "Blue[AVG]," "Blue[SD]," "Diff[AVG]," "Diff[SD]," "√Area," "SD[RED]," "SD[BLUE]," "Ratio[UPPER]," and "Ratio[BOTTOM]") were used.

The threshold or the like of each feature value is as follows

Threshold of "√Area": "43."
Radius R of "SD[RED]": "5."
Pixel region of "Ratio[UPPER]": upper 220 pixels in analysis target region.
Threshold of "Ratio[UPPER]" (foregoing (b)): "92."
Threshold of "Ratio value" of "Ratio[UPPER]" (foregoing (c): "1.15."
Pixel region of "Ratio[BOTTOM]": lower 300 pixels in analysis target region, others such as the threshold are the same as those of "Ratio[UPPER]."

Further, in Example 1, as in Comparative example 1, in order to avoid that the quality of the result of the correct value caused by a combination of files selected by chance influenced the evaluation of the established model, a trial in which 31 images for learning of each type were randomly selected and the remaining 15 images were used as the images for testing for evaluation was performed a total of 10 times, and the average value thereof was used to determine the quality of model.

Figure 5:
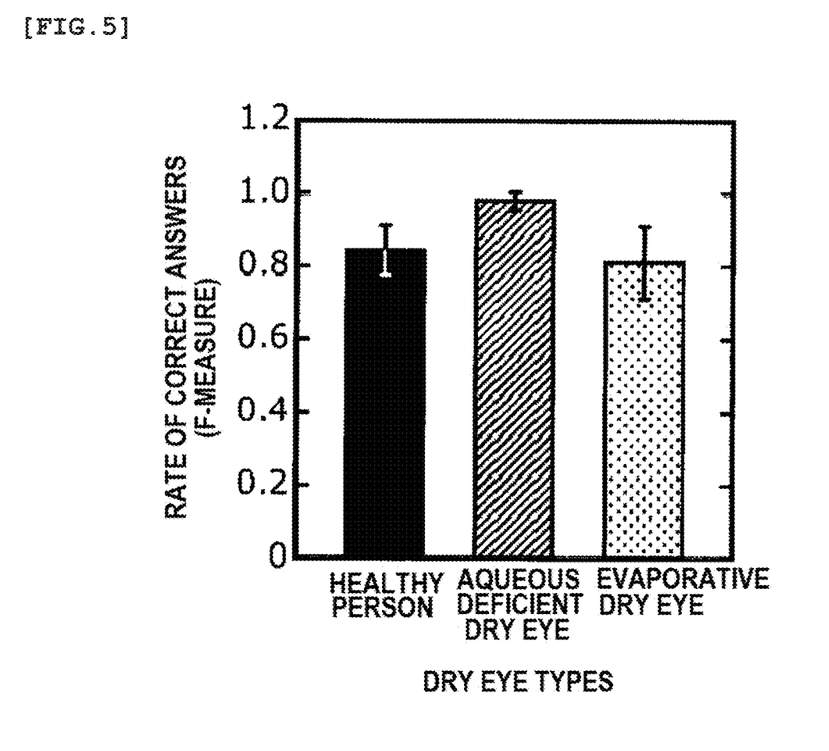
FIG. 5 is a graph indicating F-measure based on a classification result in Example 1 according to the present invention.

The classification result of Example 1 is shown in FIG. 5. The concrete numerical values of F-measure in Example 1 are as follow, "healthy person: 0.845," "ADDE: 0.981," and "EDE: 0.815." Further, the kappa coefficient (as described in Comparative example 1) in the present Example was "0.820," indicating a near-perfect model.

Example 2

A clinical trial using the machine learning model established in Example 1 was performed to confirm whether the present model was useful for the diagnosis of the dry eye types. In this trial, 46 images still images) of each type, a total of 138 images, used. in Example 1 were used as the images for learning, and the classification device performed the above learning by the method described in Example 1. All images were used because the rate of correct answers increased when more images were used.

As the test images to be classified, a total of 100 moving images having a more recent acquired date than the images for learning were prepared (breakdown of images: 33 moving images of "healthy person," 33 moving images of "ADDE," 34 moving images of "EDE"). From each moving image, ten images at an interval of 0.5 seconds within 5 seconds after the eyelid opening were cut out as still images and subjected to the type determination (type classification) of the dry eye.

As evaluation criteria of the classification, the most frequent type in the determination results obtained using a total of 5 images from 3 seconds to 5 seconds after the eyelid opening, that is, the latter half of the 10 images at the interval of 0.5 seconds within 5 seconds after the eyelid opening, was regarded as the classification result of the test images. For example, in a case where the determination result of the 5 images was "healthy person/EDE/EDE/EDE/healthy person," the test images were classified as the most frequent "EDE."

Figure 6:
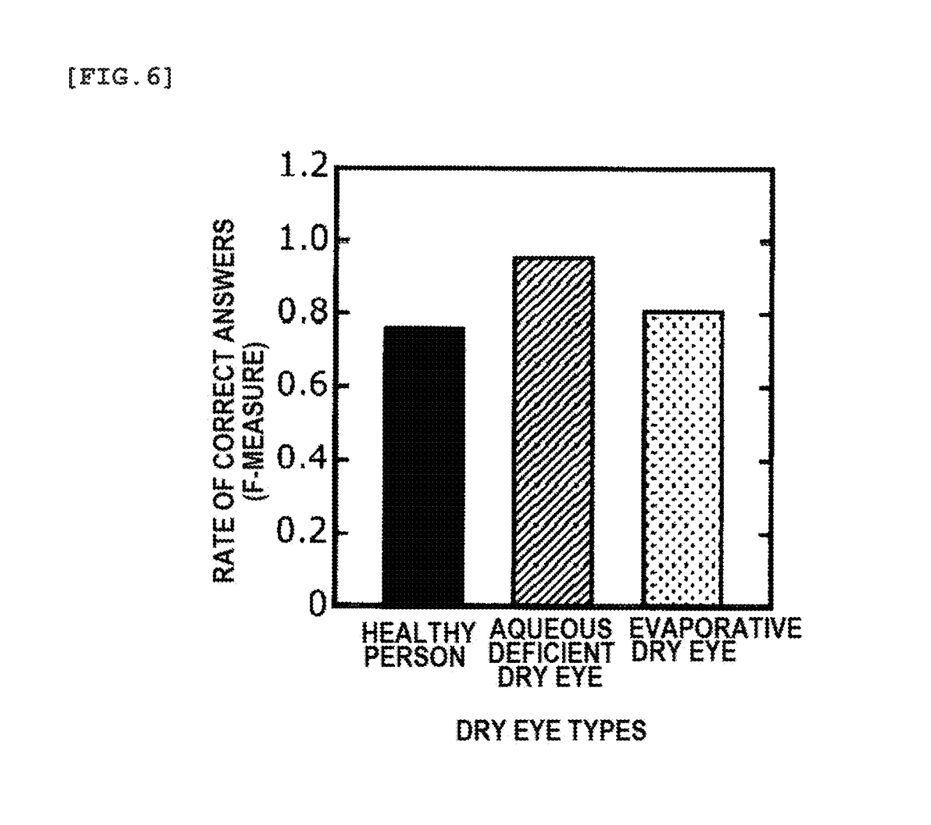
FIG. 6 is a graph indicating F-measure based on a classification result in Example 2 according to the present invention.

The above-described result is shown in FIG. 6. The concrete numerical values of F-measure in the present Example are as follow, "healthy person: 0.762," "ADDE: 0.954," and "EDE: 0.806." Further, in the present. Example, the kappa coefficient calculated as true agreement with a diagnostic result by a doctor, thereby eliminating a coincidence, was "0.760," indicating that the present machine classification model was very effective in the dry eye type diagnosis.

Although the present invention has been described above, the present invention is not limited to the foregoing description and Examples in the foregoing description, as a primary use application of the present invention, the classification. of the dry eye types was mentioned and described. However, the use application of the present invention is not limited thereto. In a case where the present invention is applied other than to the classification of the dry eye types, an appropriate parameter (feature value) may be selected and used in accordance with the use application.

Regarding the interference fringe image of tear fluid layer, in Example 1, the plurality of still images are prepared as the image for learning and the test image to be classified. On the other hand, in Example 2, the moving image is prepared as the test image to be classified and the still images are used as the image for learning. As described above, the image as a testing object may be a still image or a moving image. Further, the still image may be cut out from the reproducing moving image (the moving image to be reproduced may be a moving image for live broadcasting or a recorded moving image) at a time point indicated by a doctor and added to the image for learning. In the case where the still image cut out from the moving image was used as the image for learning, a frame may be freely cut out and the cut-out frame may be subjected to a predetermined arithmetic operation, for example, color correction, out of focus correction, removal of a region where is not necessary for analysis, and the like, and then used.

INDUSTRIAL APPLICABILITY

According to the present invention, it becomes possible to objectively and automatically perform the classification of the interference fringe image of tear fluid layer by the dry eye types, and thus the present invention is expected to provide an objective index for the diagnosis of the dry eye types.

The invention claimed is:
1. An image classification method comprising:
a step of acquiring a feature value from an interference fringe image of tear fluid layer for learning;
a step of constructing a model for classifying an image from the feature value acquired from the interference fringe image of tear fluid layer for learning;
a step of acquiring the feature value from an interference fringe image of tear fluid layer for testing; and
a step of performing classification processing for classifying the interference fringe image of tear fluid layer for testing by types of dry eye using the model and the feature value acquired from the interference fringe image of tear fluid layer for testing.

2. The image classification method according to claim 1, wherein the feature value is information relating to a color of the image and includes at least one piece of information relating to a color, color diversity, color brightness, and local color variation.

3. The image classification method according to claim 2, wherein the information relating to the color is information based on a luminance average of at least one of red and blue luminance images.

4. The image classification method according to claim 2, wherein the information relating to the color diversity is information based on a standard deviation of a luminance of at least one of red and blue luminance images.

5. The image classification method according to claim 2, wherein the information relating to the color brightness is information based on a difference value of luminances of pixels.

6. The image classification method according to claim 2, wherein the local color variation is information based on a standard deviation calculated from a luminance of a pixel of interest and a luminance of a pixel adjacent thereto.

7. The image classification method according to claim 1, wherein in a case where the interference fringe image of tear fluid layer for testing is a moving image, a plurality of predetermined frames are subjected to the classification processing and a most frequent result is regarded as a classification result of the image for testing.

8. The image classification method according to claim 1, wherein the feature value is acquired from a predetermined region of the interference fringe image of tear fluid layer for learning and the interference fringe image of tear fluid layer for testing.

9. The image classification method according to claim 1, wherein the interference fringe image of tear fluid layer for testing is a moving image within a predetermined period of time subsequent to eyelid-opening detection or one or more still images acquired at an optional timing within a predetermined period of time subsequent to eyelid-opening detection.

10. The image classification method according to claim 9, wherein the predetermined period of time is 5 seconds.

11. An image classification device configured to execute the method according to claim 1.

12. An image classification program stored in a non-transitory computer readable medium for making a computer to execute the method according to claim 1.

* * * * *